(12) United States Patent
Sajda et al.

(10) Patent No.: US 7,835,787 B2
(45) Date of Patent: Nov. 16, 2010

(54) SINGLE TRIAL DETECTION IN ENCEPHALOGRAPHY

(75) Inventors: Paul Sajda, New York, NY (US); Lucas Cristobal Parra, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1797 days.

(21) Appl. No.: 10/966,290

(22) Filed: Oct. 15, 2004

(65) Prior Publication Data

US 2009/0326404 A1 Dec. 31, 2009

Related U.S. Application Data

(63) Continuation of application No. PCT/US03/13943, filed on May 5, 2003.

(60) Provisional application No. 60/377,833, filed on May 3, 2002.

(51) Int. Cl.
*A61B 5/04* (2006.01)
(52) U.S. Cl. ..................... 600/544; 600/545
(58) Field of Classification Search ............. 600/300, 600/544–547
See application file for complete search history.

(56) References Cited

U.S. PATENT DOCUMENTS

RE34,015 E * 8/1992 Duffy .................. 600/544

5,269,325 A * 12/1993 Robinson et al. ............ 600/409

OTHER PUBLICATIONS

Tang et al., "Independent Components of Magnetoencephalography: Localization," Neural Computation, Neural Comput. 14 (8): 1827-1858 (2002).
Gehring, W. J. et al., "The medical frontal cortex and the rapid processing of monetary gains and loss," Science, 295: 2279-2282 (2002).
Pfurtscheller, G. et al., "Motor imagery and direct brain-computer communication," Proceedings of the IEEE, 89 (7): 1123-1134 (2001).
Baillet, S. et al., "Electromagnetic brain mapping." IEEE Signal Processing Magazine, 18(6): 14-30 (2001).
Boas et al., "Imaging the body with diffuse optical tomography." IEEE Signal Processing Magazine, 18 (6): 57-75 (2001).
Falkenstein, M. et al., "ERP components on reaction errors and their functional significance : a tutorial," Biological Psychology, 51: 87-107 (2000).
Schalk et al., "EEG-based communication : presence of an error potential," Clinical Neurophysiology, 111: 2138-2144 (2000).
Vigario et al., "Independent component approach to the analysis of EEG and MEG recordings," IEEE Transactions on Biomedical Engineering, 47(5): 589-593 (2000).

(Continued)

*Primary Examiner*—Robert L Nasser
*Assistant Examiner*—Michael D'Angelo
(74) *Attorney, Agent, or Firm*—Baker Botts LLP

(57) ABSTRACT

An EEG cap (8) having 64 or 128 electrodes (10) is placed on the head of the subject (11) who is viewing CRT monitor (14). The signals on each channel are amplified by amplifier (17) and sent to an analog-to-digital converter (20). PC (23) captures and records the amplified signals and the signals are processed by signal processing PC (26) performing linear signal processing. The resulting signal is sent back to a feedback/display PC (29) having monitor (14).

14 Claims, 4 Drawing Sheets

OTHER PUBLICATIONS

Ramoser et al., "Optimal spatial filtering of single trial EEG during imagined hand movement," IEEE Transaction on Rehabilitation Engineering, 8 (4): 441-446 (2000).

Andersen et al., "Multivariate Autoregressive Models for Classification of Spontaneous Electroencephalogram During Mental Tasks," IEEE Transactions on Biomedical Engineering, 45 (3): 277- 286 (1998).

Porro et al., "Primary motor and sensory cortex activation during motor performance and motor imagery: a functional magnetic resonance imaging study," The Journal of Neuroscience, 16 (23): 7688-7698 (1996).

Makeig et al., "Independent component analysis of electroencephalographic data," Advances in Neural Information Processing Systems, 8: 145-151, MIT Press (1996).

Cunnington et al., "Movement-related potentials associated with movement preparation and motor imagery," Exp. Brain Res., 111 (3): 429-436 (1996).

Coles M. G. H. et al., "Event-related brain potentials: an introduction," Electrophysiology of Mind Oxford: Oxford University Press (1995).

Dehaene et al., "Localization of a neural system for error detection and compensation," Psychological Science, 5: 303-305 (1994).

Gehring, W. J. et al., "A neural system for error detection and compensation," Psychological Science, 4 (6): 385-390 (1993).

Towle et al., "The spatial location of EEG electrodes: locating the best-fitting sphere relative to cortical anatomy," Electroencephalogr Clin. Neurophysiol., 86(1) : 1-6 (1993).

Swets, "ROC analysis applied to the evaluation of medical imaging techniques," Iravestigative Radiology 14: 109-121 (1979).

* cited by examiner

SINGLE TRIAL DETECTION IN ENCEPHALOGRAPHY

CROSS-REFERENCE TO RELATED APPLICATION

The present application is a continuation of International Patent Application No. PCT/US03/13943, filed May 5, 2003, published on Nov. 13, 2003 as International Patent Publication No. WO 03/093947, which claims priority to U.S. Provisional Patent Application No. 60/377,833, filed on May 3, 2002, the entire disclosure of which is incorporated herein by reference.

NOTICE OF GOVERNMENT RIGHTS

The U.S. Government has certain rights in this invention pursuant to the terms of Defense Advanced Research Project Agency (DARPA) contract N00014-010C-0482 and the Department of Defense Multidisciplinary University Research Initiative (MURI) program administered by the Office of Naval Research under Grant N00014-01-1-0625.

BACKGROUND OF INVENTION

The performance of a brain computer interface (BCI) can be optimized by considering the simultaneous adaptation of both a human and machine learner. Preferably, adaptation of both learners occur on-line and in (near) real-time. The human and machine learners are assumed to process data sequentially, with the human learner gating the response of the machine learner. The gating by the human learner captures the dynamic switching between task-dependent strategies, while the machine learner constructs the mappings between brain signals and control signal for a given strategy (or set of strategies). The human and machine co-learn in that they adapt simultaneously to minimize an error metric, or equivalently, maximize a bit rate.

In a typical BCI system, signal acquisition from a human learner, or subject, is typically through one or more modalities (electroencephalography (EEG), magnetoencephalography (MEG), chronic electrode arrays, etc.). A key element of a BCI system is a machine learning or pattern recognition module to interpret the measured brain activity and map it to a set of control signals or, equivalently, a representation for communication, e.g., a visual display.

In addition to the machine learner, the human learner is integral to a BCI system. Adaptation of the human learner is often implicit, for example humans will switch strategies (e.g. think left/right versus up/down) based on their perceived performance. This dynamic switching by the human learner can make adaptation of the machine learner challenging, particularly since this can be viewed as making the input to the machine learner more non-stationary. Since the overall challenge in BCI is to maximize performance of the combined human-machine system (i.e., minimize error rate or conversely maximize bit rate) an approach is required which jointly optimizes the two learners.

Conventional analysis of brain activity using EEG and MEG sensors often relies on averaging over multiple trials to extract statistically relevant differences between two or more experimental conditions. Trial averaging is often used in brain imaging to mitigate low signal-to-interference (SIR) ratios. For example, it is the basis for analysis of event-related potentials (ERPs) as explained in Coles M. G. H. et al., "Event-related brain potentials: An introduction," *Electrophysiology of Mind*. Oxford: Oxford University Press (1995).

However, for some encephalographic applications, such as seizure prediction, trial averaging is problematic. One application where the problem of single-trial averaging is immediately apparent is the brain computer interface (BCI), i.e., interpreting brain activity for real-time communication. In the simplest case, where one wishes to communicate a binary decision, averaging corresponds to asking the same question over multiple trials and averaging the subject's binary responses. In order to obtain high-bandwidth communication, it is desirable to do as little averaging over time or across trials as possible.

More generally, single-trial analysis of brain activity is important in order to uncover the origin of response variability, for instance, in analysis of error-related negativity (ERN). The ERN is a negative deflection in the EEG following perceived incorrect responses (Gehring, W. J. et al., "A neural system for error detection and compensation," *Psychological Science*, 4(6):385-390 (1993); Falkenstein, M. et al., "ERP components on reaction errors and their functional significance: A tutorial," *Biological Psychology*, 51:87-107, (2000) or expected losses (Gehring, W. J. et al., "The medical frontal cortex and the rapid processing of monetary gains and loss," *Science*, 295: 2279-2282 (2002)) in a forced-choice task. Single-trial detection of the ERN has been proposed as a means of correcting communication errors in a BCI system (Schalk et al., "EEG-based communication: presence of an error potential," *Clinical Neurophysiology*, 111:2138-2144, (2000)). With the ability to analyze the precise timing and amplitude of the ERN, on individual trials, one can begin to study parameters that cannot be controlled across trial, such as reaction time or error perception. Such an approach opens up new possibilities for studying the behavioral relevance and neurological origin of the ERN.

With the large number of sensors on a single subject in high-density EEG and magnetoencephalography (G), e.g., 32 or more sensors, an alternative approach to trial averaging is to integrate information over space rather than across trials. A number of methods along these lines have been proposed. Blind source separation analyzes the multivariate statistics of the sensor data to identify spatial linear combinations that are statistically independent over time (Makeig et al., "Independent component analysis of electroencephalographic data," *Advances in Neural Information Processing Systems*, 8: 145-151, MIT Press (1996); Vigario et al., "Independent component approach to the analysis of EEG and MEG recordings," *IEEE Transactions on Biomedical Engineering*, 47(5): 589-593 (2000); Tang et al., "Localization of Independent Components of Magnetoencephalography in Cognitive Tasks," *Neural Computation, Neural Comput.* 14(8): 1827-1858 (2002)). Separating independent signals and removing noise sources and artifacts increases SIR. However, blind source separation does not exploit the timing information of external events that is often available. In most current experimental paradigms subjects are prompted with external stimuli to which they are asked to respond. The timing of the stimuli, as well as the timing of overt responses, is therefore available, but is generally not exploited by the analysis method.

In the context of a BCI system, many methods have applied linear and nonlinear classification to a set of features extracted from the EEG. For example, adaptive autoregressive models have been used to extract features across a limited number of electrodes, with features combined using either linear or nonlinear classifiers to identify the activity from the time course of individual sensors (Pfurtscheller, G. et al., "Motor imagery and direct brain-computer communication," *Proceedings of the IEEE*, 89(7):1123-1134, (2001)). Others have proposed to combine sensors in space by computing maximum and minimum eigenvalues of the sensor covariance matrices. The eigenvalues, which capture the power variations of synchronization and desynchronization, are then combined nonlinearly to obtain binary classification (Ramoser et al., "Optimal spatial filtering of single trial EEG during imagined hand movement," *IEEE Transaction on Rehabilitation Engineering*, 8(4):441-446 (2000)). Spatial filtering has also been used to improve the signal-to-noise ratio (SNR) of oscillatory activity. However, there has been no systematic effort to choose optimal spatial filters. In the context of the ERN, Gehring et al. (1993) use linear discrimination to identify characteristic time courses in individual electrodes, but do not exploit spatial information. Although many of these aforementioned methods obtain promising performance in terms of classifying covert (purely mental) processes, their neurological interpretation remains obscured.

SUMMARY OF INVENTION

It is therefore an object of this invention to provide a system and method which will maximize performance of a BCI.

It is a further object of this invention to provide a system and method which will yield good single trial discrimination in a relatively short period of time.

These and other objects are accomplished by use of conventional linear discrimination to compute the optimal spatial integration of a large array of brain activity sensors. This allows exploitation of timing information by discriminating and averaging within a short time window relative to a given external event. Linear integration permits the computation of spatial distributions of the discriminating component activity, which in turn can be compared to functional neuroanatomy to evaluate the validity of the result. The term "component" instead of "source" is preferred so as to avoid confusion with an implied physiological source.

BRIEF DESCRIPTION OF THE DRAWINGS

Further objects, features, and advantages of the present invention will become apparent from the following detailed description taken in conjunction with the accompanying drawings showing illustrative embodiments of the present invention, in which.

DETAILED DESCRIPTION OF THE INVENTION

Figure 1:
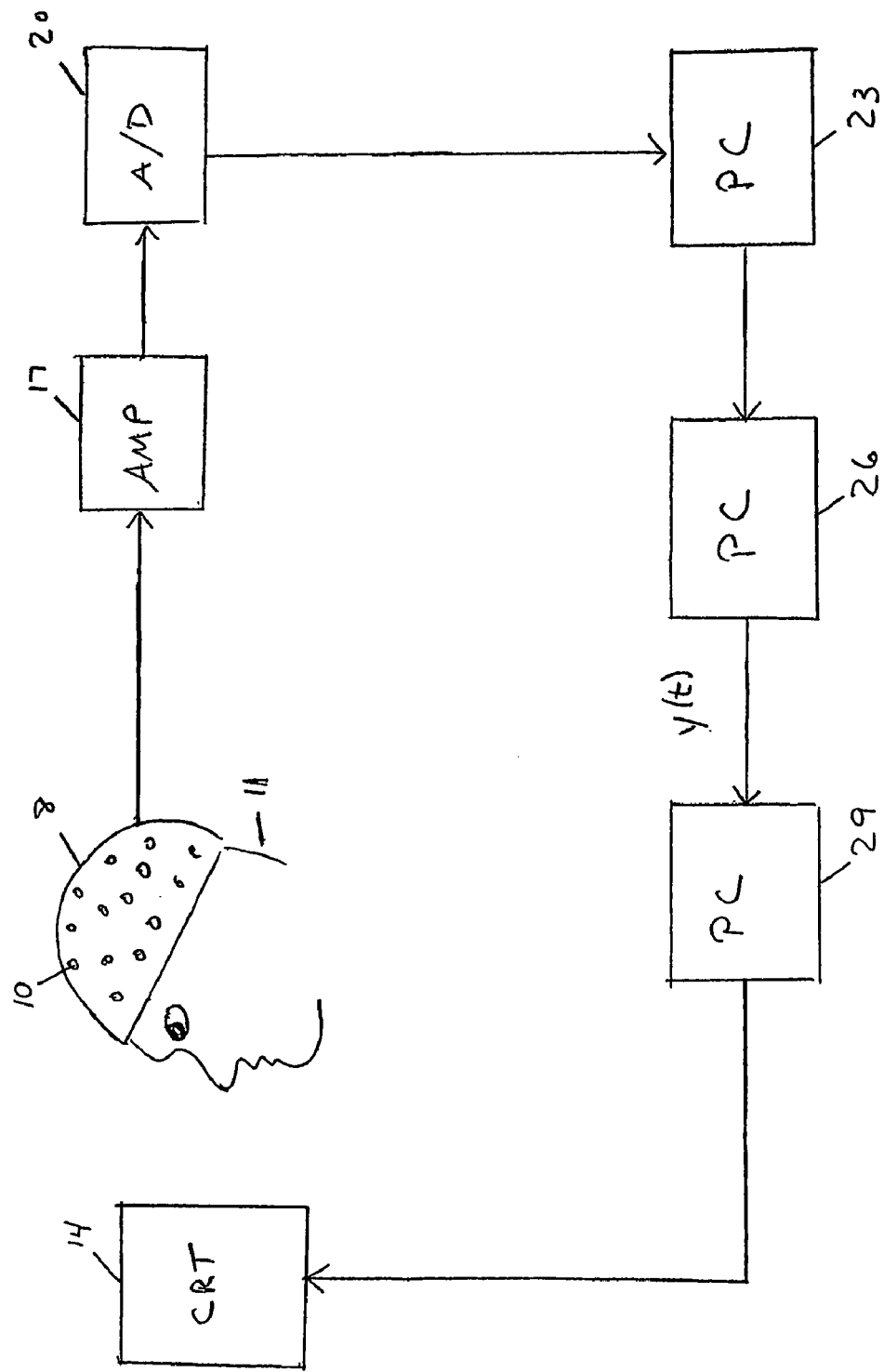
FIG. 1 is a block diagram of an exemplary embodiment of the system of the present invention.
Figure 2:
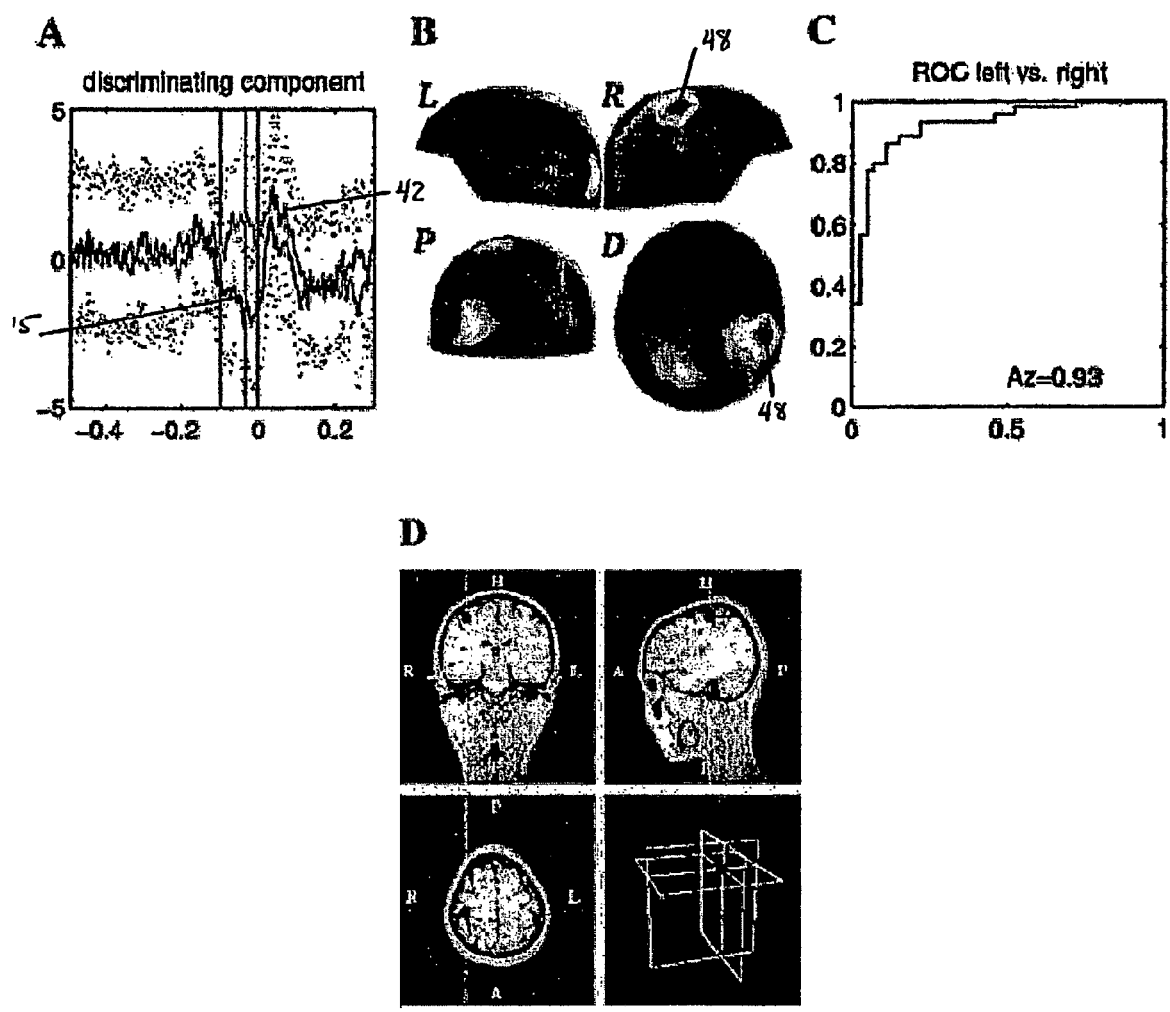
FIG. 2 shows the results of a test using the present invention which predicts explicit (overt) motor response using 122 MEG sensors.

An exemplary embodiment of the system of the present invention is shown in FIG. 1. An EEG cap 8 is placed on the head of a subject 11 who is viewing CRT monitor 14. The cap, such as available from Electro-Cap, Inc., may have any number of Ag/AgCl electrodes 10, with 64 or 128 electrodes, and a like number of corresponding output channels, being preferred. The signals on each channel are amplified by amplifier 17 and sent to analog-to-digital converter 20. From there, data acquisition PC 23 captures and records the amplified signals using commercially-available data acquisition software, such as Cogniscan™, available from Cognitronics, Inc., which can also provide lowpass/bandpass filtering. The signals are then processed by signal processing PC 26 which performs the linear signal processing described below. Appendix A provides exemplary software in accordance with the present invention for the signal processing PC 26. The resulting signal is sent to a feedback/display PC 29 having monitor 14. PCs 23, 26, 29 may each be a Dell 530, 2.4 GHz, or equivalent model. It will be understood that the functions of any two or all of PCs 23, 26, 29 may be combined into a single computer.

The signal processing performed by signal processing PC 26 may be broken into two types—linear discrimination and localization of discriminating components.

Linear Discrimination

As described below, a logistic regression model is used to learn an optimal linear discriminator using the spatial distribution of EEG activity across a high-density sensor array. Denoting x(t) as the M sensor values sampled at time instance t, spatial weighting coefficients v are computed such that $$y(t) = v^T x(t) \quad (1)$$

is maximally discriminating between the times t, corresponding to two different experimental conditions. For example, in the prediction of explicit motor response experiments (an example of which is described below in Example I) the times correspond to a number of samples prior to an overt button push. The samples corresponding to a left button push are to be discriminated from samples of a right button push. For each of N trials there may be T samples totaling NT training examples. Conventional logistic regression (Duda et al., *Pattern Classification*, John Wiley & Sons, 2nd Edition, (2001), incorporated herein by reference) is used to find v. A number of other linear classifiers were tested, including support vector machines (SVM) and perceptron, (id.), as well as Gaussian classifiers, and all had essentially the same performance. After finding the optimal v we average over the T dependent samples of the kth trial to obtain a more robust result, $$\bar{y}_k = \frac{1}{T} \sum_{t \in T_k} y(t),$$

where $T_k$ denotes the set of sample times corresponding to trial k. Receiver operating characteristic (ROC) analysis (Swets, "Analysis applied to the evaluation of medical imaging techniques," *Investigative Radiology* 14:109-121, (1979)) is done using these single-trial short-time averaged discrimination activities ($\bar{y}_k$). For visualization purposes, it is also useful to compute the trial averaged discrimination activities $$\bar{y}_e = \frac{1}{N} \sum_{k \in N_e} y_k(t) \quad (2)$$

where $N_e$ denotes the set of samples for event e (e.g. left or right button push) with time measured relative to some common reference across trials. The separation of the means together with their corresponding variances gives an indication of whether single-trial discrimination is plausible within the analysis window.

Localization of Discriminating Components

In order to provide a functional neuroanatomical interpretation of the resultant spatial weighting, a forward linear model is used to determine "sensor projections" of the discriminating component activity. In this model, y(t) is treated as a source which is maximally discriminating given the linear model and task. A simple way of visualizing the origin of a source's activity is to display the coupling coefficients of the source with the sensors. The strength of the coupling roughly indicates the closeness of the source to the sensor as well as its orientation. The coupling a is defined as the coefficients that multiply the putative source y(t) to give its additive contribution $x_y(t)$ to the sensor readings, $x_y(t)=ay(t)$. However, $x_y(t)$ is not observable in isolation; instead we observe, $x(t)=x_y(t)+x_y'(t)$, where $x_y'(t)$ represents the activity that is not due to the discriminating component. If the contributions, $x_y'(t)$, of other sources are uncorrelated with y(t) we obtain the coupling coefficients by the least-squares solution (Haykin, *Adaptive Filter Theory*, Englewood Cliffs, N.J., Prentice-Hall, (1996)). Arranging the samples x(t) for different t as columns in the a matrix X, and y(t) as a column vector y the solution is given by $$a = \frac{Xy}{y^T y} \quad (3)$$

In general other sources are not guaranteed to be uncorrelated with the discriminating component. Therefore a represents the coupling of all component activities that are correlated to the discriminating component y(t). We refer to a as a "sensor projection," as it measures the activity in the sensors that correlate with a given component. Our approach relies on the linearity of y(t) and the fact that different sources in EEG and MEG add linearly (Baillet, S. et al., "Electromagnetic brain mapping." *IEEE Signal Processing Magazine*, 18(6): 14-30, 2001).

Sensor projection a was derived as follows. Assuming the observation vector is x, a linear classifier, $y_1 = v^T x$, can be built where $y_1$ is the binary number indicating some cognitive event that we are trying to detect. A number of such cognitive events occurring simultaneously is assumed. These are represented as a vector of binary indicators y, with $y_1$ as its first element, and a matrix A that maps these to the observation vectors; i.e., x=Ay. Without restriction y is normalized to be zero mean. We wish to identify this mapping, namely to find the first column of A, which we call a and which is defined as the observation vector that would be obtained if only $y_1$ occurred. The most likely a can be found as follows. Let X be the zero mean observation matrix for many samples, i.e., the $t^{th}$ column is the observation for the $t^{th}$ sample. Let $y_1^T$ be the corresponding binary column vectors across these samples given by $y_1 = v^T X$. The definition for a implies $X = ay_1$. The maximum likelihood estimate for a, given v and X, is given by the least-squares solution, $a = Xy_1^T(y_1 y_1^T)^{-1}$. We would like to determine the conditions under which the least-squares estimate of a is actually proportional to the first column of A. Let the matrix Y be the binary matrix of the simultaneous cognitive events across trials, i.e., the $t^{th}$ column is the cognitive events vector y for the $t^{th}$ trial. Since X=AY, we find that $a = AYy_1^T(y_1 y_1^T)^{-1}$. Note that Y has dimensions of number of cognitive events (N) by number of samples (T), and that the quantity $Yy_1^T$ is the column vector of unnormalized correlations between the event indicators $y_1$ and the set of all cognitive events. If this is proportional to the Kronecker delta, $\delta_{i,1}$ (i.e., $y_1$ is uncorrelated with the indicators of the other events), then $\alpha_i \propto \Sigma_j A_{i,j} \delta_{i,1} = A_{i,1}$, and therefore a is proportional to the first column of A.

EXAMPLES

Example I

Predicting explicit (overt) motor response using MEG: Four subjects performed a visual-motor integration task. A "trump" experiment was defined whereby subjects were simultaneously presented with two visual stimuli on a CRT, one of which is the target and "trumps" (beats-out) the other. Subjects were instructed to push a left hand or right hand button, depending on which side the target (trump stimulus) was present. The subject was to discover the target by trial and error using auditory feedback. Each trial began with visual stimulus onset, followed by button push, followed by auditory feedback, indicating if the subject responded correctly. The interval between the motor-response and the next stimulus presentation was 3.0±0.5 sec. Each subject performed 90 trials, which took approximately 10 minutes. MEG data was recorded using 122 sensor at a sampling rate of 300 Hz and high-pass filtered to remove DC drifts. Dipole fits were done using the "xfit" tools available from Neuromag (www.neuromag.com), which assume a spherical head model to find a single equivalent current dipole.

Example II

Classifying imagined (covert) motor activity using EEG: Nine subjects performed a visual stimulus driven finger (L/R) tapping task. Subjects were asked to synchronize an explicit or imagined tap by the left, right, or both index fingers to the presentation of a brief temporally predictable signal. Subjects were trained until their explicit taps occurred consistently within 100 ms of the synchronization signal. Subjects were presented visual stimuli indicating with which index finger to tap and if it should be an explicit or imagined tap. 1.25 seconds after the last instruction symbol a fixation point was replaced for 50 ms by the letter "X." This letter served as a signal to which the instructed tap (whether overt or imagined) was to be synchronized. Each trial lasted for 6 s. After training, each subject received 10 blocks of trials. Each 72-trial block consisted of nine replications of the eight trial types (Explicit vs. Imagined×Left vs. Right vs. Both vs. No Tap) presented in a random order. Trials with noise due to eye blinks were not considered in the EEG analysis. The electromyogram (EMG) was recorded to detect muscle activity during imagined movements. The 59 EEG channels were sampled at 100 Hz and high-pass filtered to remove DC components.

Example III

Detection of decision errors from EEG: Seven subjects performed a visual target detection amongst distractors task. On each trial, subjects were presented with a stimulus for 100 ms. There were four possible stimuli, each consisting of a row of five arrows. Subjects were told to respond by pressing a key on the side indicated by the center arrow. They were to ignore the four flanking arrows. On half of the trials, the flanking arrows pointed in the same direction as the target (e.g. <<<<<), on the other half the flankers pointed in the opposite direction (e.g. <<><<). Subjects were slower and made many more errors in the latter case. Following their response, there was an inter-trial interval of 1.5 seconds, after which a new stimulus was presented. Subjects performed 12 blocks of 68 trials each. The 100 ms interval prior to the response was used as the baseline period (separately for each trial and electrode). The sampling rate was 250 Hz. Following the baseline period, trials were manually edited to remove those with blinks, large eye movements, instrument artifacts and amplifier saturation.

Results

Single trial discrimination results are shown for Examples I-III and include trial averaged discriminating component activity $\bar{y}_e(t)$, sensor projections a, and detection/prediction performance using single-trial, short-time averaged $\bar{y}_k$. Performance is reported using ROC analysis computed with a leave-one-out traning and testing procedure (Duda et al. (2001). ROC analysis is a reasonable method for quantifying performance for these three data sets, since it enables one to incorporate an independent cost for false positives and false negatives. For example, in an error correction application using the ERN, it is important to detect error events with high confidence. The desired operating point of such a detector is therefore at a low false-positive rate (high specificity). In contrast, an application which looks to exploit motor imagery for communicating a binary decision is best assessed at the operating point where sensitivity equals specificity; i.e. the error rates for the two possible outcomes are equal. A metric that quantifies the overall performance of a detector for arbitrary operating points is the area under the ROC curve ($A_z$). Below we report $A_z$ as well as the fraction of correct classification for all three tasks. A summary of the results for the three examples is given in the following table, where mean and standard deviation (SD) are reported across N subjects; $N_e$ is the number of trials used to determine the best linear classifier (no. positive/no. negative trials):

(A) shows trial averages $\bar{y}_e(t)$ (solid curves 42, 45) and standard deviations (dotted curves) of discriminating component for left and right button pushes, curves 42 and 45, respectively. Time is indicated in seconds. The vertical line at t=0 s indicates the timing of the button push. The vertical lines earlier in time mark the discrimination window. One can see significant separation of the means for left vs. right button push within the analysis window. Given that this separation is approximately equal to one standard deviation, this suggests that single trial discrimination is possible. (B) shows the sensor projections for the discrimination vector. Area 48 shows the highest activity. (C) shows the ROC curve for left vs. right discrimination. The area under the curve $A_z$ is 0.93, indicating good single-trial discriminability. (D) shows the dipole-fit of a overlaid on an MRI image. A single equivalent current dipole fits the data with an accuracy of 64% using the least squares 'xfit' routine from Neuromag. This compares favorably with the 50% goodness of fit which are typically obtained for somatosensory responses when using all 122 sensors (Tang 2002). When considered with respect to the motor-sensory homunculus, these results indicate that the discrimination source activity originates in the sensory-motor cortex corresponding to the left hand.

Figure 4:
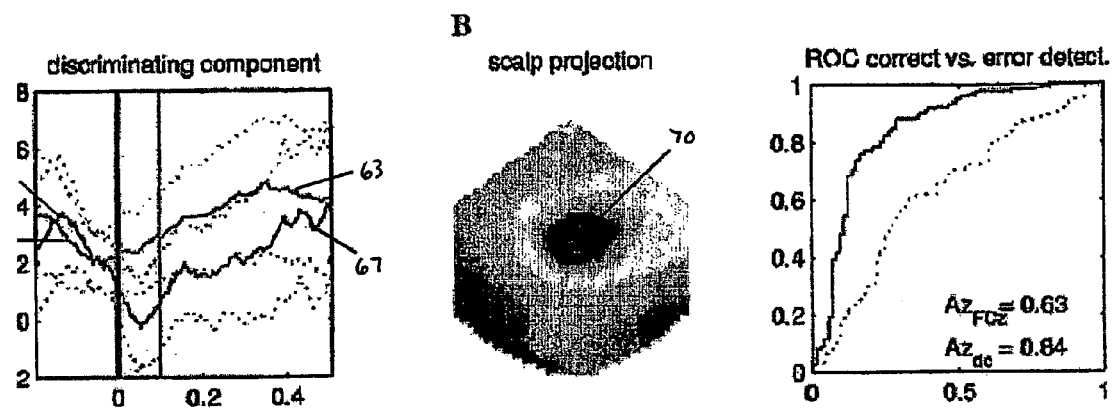
FIG. 4 shows the results of a test using the present invention which detects decision errors for a binary discrimination task using 64 EEG sensors.

FIG. 4 shows results for the Example II data set, where the goal is to detect activity associated with purely imagined motor response, a situation more realistic for a BCI system. Subjects are trained to imagine a tap with the left or right index finger synchronized to a brief, temporally predictable signal. Therefore there exists a known time window in which we can explicitly look for activity that discriminates between the left and right imagine conditions. A 0.8 s time window around the time where the task is to be performed was selected. 90 left and 90 right trials were available to train the

| | ROC area ($A_z$) mean ± SD | Fraction correct Mean ± SD | N | $N_e$ | Sensors | Detection time window |
|---|---|---|---|---|---|---|
| Explicit L/R button push prediction | 0.82 ± 0.06 | 0.79 ± 0.09 | 4 | 45/45 | 122 MEG | 100 ms to 33 ms prior to button push |
| Imagined L/R finger tap discrimination | 0.77 ± 0.10 | 0.71 ± 0.08 | 9 | 90/90 | 59 EEG | 400 ms before to 400 ms after synchronization |
| Response error/correct discrimination | 0.79 ± 0.05 | 0.73 ± 0.05 | 7 | 40-80/300 | 64 EEG | 0 ms to 100 ms after response |

As seen in Table 1, for all three data sets the number of trials for training is comparable to the number of coefficients to be trained. This can lead to serious problems in overtraining. We mitigate these by including multiple training samples for each trial. These samples are obviously not independent; however, they provide evidence for the natural variation of the data and thus make the estimates much more robust. They were shown, through cross-validation, to improve estimated generalization performance. We would expect that increasing the number of independent training samples (e.g., trials) would similarly increase performance of the results presented below.

Figure 3:
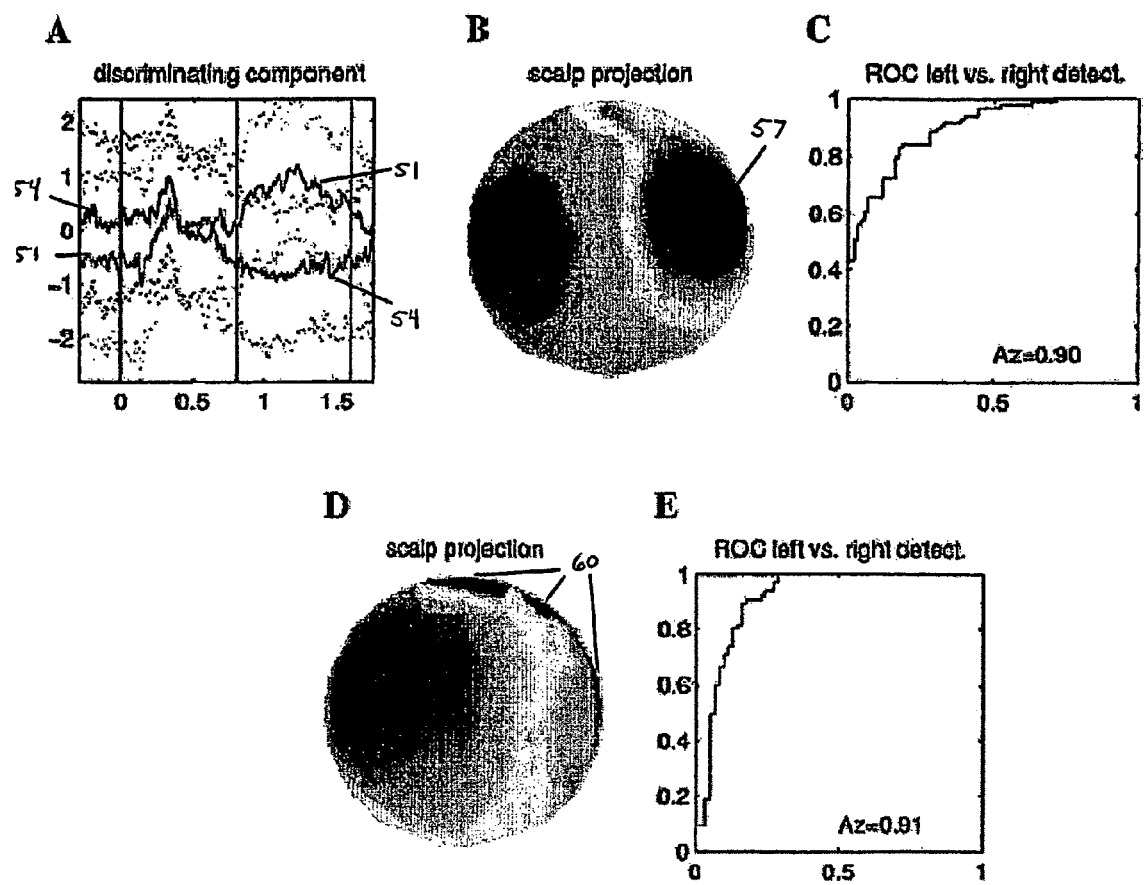
FIG. 3 shows the results of a test using the present invention which classifies imagined (covert) motor activity using 59 EEG sensors.

FIG. 3 shows results for the Example I data set used to predict whether a subject will press a button with their left or right hand by analyzing the MEG signals in a window prior to the button push (left hand=1, right hand=0 in the logistic regression model). We use an analysis window 100 ms wide centered at 83 ms prior to the button event, which at 300 Hz corresponds to T=30. FIG. 3 shows the results for one subject.

coefficients of the 59 EEG sensors. The results for the best performing subject is $A_z$=0.90. (A) shows trial averages $\bar{y}_e(t)$ (solid curves 51, 54) and standard deviations (dotted curves) of discriminating component for left and right imagined taps, curves 51 and 54, respectively. The vertical solid line at t=0 seconds indicates the timing of the visual stimulus that defines the action to be performed (left or right imagine). The subjects are trained to execute the task at around t=1.25 s. The vertical lines after t=0 indicate the discrimination window. (B) shows a dorsal view of sensor projections a. Area 57 has the highest activity. (C) shows the ROC curve for left vs. right discrimination. For this subject the fraction of correct classification is p=0.79 which corresponds to an information transfer of 0.26 bits/trial. (D) shows sensor projection of discriminating component for explicit finger tap. Areas 60 have highest activity. (E) shows the ROC curve for the same subject for an explicit finger tap.

The sensor projection of the 59 EEG sensors shows a clear left-right polarization over the motor area. In the context of BCI the metric of interest is the bit rate of at which information can be transmitted with imagined motor activity. The information transmitted per trial is given by, $$I = 1 + p \log_2(p) + (1-p)\log_2(1-p), \quad (4)$$

where p is the fraction correct. As noted above, for the subject shown in FIG. 4 this corresponds to I=0.26 bits. When averaged over the nine subjects the information transmitted is I=0.16 bit/trial. Note that with a repetition rate of 6 seconds this experiment is not designed for an optimal transmission rate. Assuming instead a repetition rate of 0.8 seconds (corresponding to the time window used here for discrimination) we obtain an average bit rate of 12 bits/minute.

For comparison, an alternative method, first described by Wolpaw et al. (1991), that is based on differences in the power spectrum in electrodes over the left and right motor cortex was also tested. Andersen et al., ("Multivariate Autoregressive Models for Classification of Spontaneous Electroencephalogram During Mental Tasks," *IEEE Transactions on Biomedical Engineering*, 45(3):277-286, (1998)) modifies the approach by using six auto-regressive (AR) coefficients to model the power spectrum of each electrode within the analysis window and classify the imagined conditions using a linear discrimination on these AR coefficients. Following Penny et al. (2000), we used electrodes C3 and C4 (international 10/20 electrode placement system—see Towle et al., "The spatial location of EEG electrodes: locating the best-fitting sphere relative to cortical anatomy," *Electroencephalogr Clin. Neurophysiol.*, 86(1): 1-6, (1993)) and obtain $A_z = 0.65 \pm 0.09$, and fraction correct of $p = 0.62 \pm 0.07$, which corresponds to I=0.054 bits/trial or a bit rate of 4 bit/minute. This is about a fourth of the results obtained with our proposed method.

The results, across the nine subjects, for predicting explicit finger taps from a window 300 ms to 100 ms prior to the taps is $A_z = 0.87 \pm 0.08$ and a fraction correct of $0.80 \pm 0.08$. As shown in FIG. 4, for one subject sensor projections of the discrimination vector for explicit motor response are similar to the projections of the imagined motor response. This is consistent with previous finding in EEG and fMRI (Cunnington et al., "Movement-related potentials associated with movement preparation and motor imagery," *Exp. Brain Res.*, 111(3):429-36, (1996); Porro et al., "Primary motor and sensory cortex activation during motor performance and motor imagery: a functional magnetic resonance imaging study," *J Neurosci.*, 16(23): 7688-98 (1996)) and supports the approach of many current BCI systems-signals arising from the cortical areas that encode an explicit movement are also in some sense optimal for detecting the imagined movement.

FIG. 5 shows the results for the target detection experiments where the goal is to detect the Error Related Negativity (ERN) on a single trial basis. The ERN has a medial-frontal distribution that is symmetric to the midline, suggesting a source in the anterior cingulate (Dehaene et al., "Localization of a neural system for error detection and compensation," *Psychological Science*, 5: 303-305, (1994)). It begins around the time of the perceived incorrect response and lasts roughly 100 ms thereafter. We, use this time window for detection. 40 to 80 error trials and 300 correct trials were used for training and testing 64 coefficients. (A) shows trial averages e(t) (solid curves 63, 67) and standard deviations (dotted curves) of the discriminating component for correct and error trials, curves 63 and 67, respectively. The negative deflection after a button push response at t=0 s is the ERN. Vertical lines at t=0 and t=100 ms indicate the discrimination window. (B) shows the dorsal view of sensor projections a. Area 70 has the highest activity. (C) shows the ROC curve for error vs. correct trials. The solid curve corresponds to discrimination using Eq. (1), and dotted line to discrimination with center electrode (FCz). The sensor projection shown in FIG. 5(B) for one subject is representative of the results obtained for other subjects and is consistent with the scalp topography and time course of the ERN. The detection performance for this subject was $A_z = 0.84$ and is to be compared to $A_z = 0.63$ when detecting ERN from the front-center electrode where maximal activity is expected (FCz in the 10/20 system).

The results of Examples I-III demonstrate the utility of linear analysis methods for discriminating between different events in single-trial, stimulus driven experimental paradigms using EEG and MEG. An important aspect of our approach is that linearity enables the computation of sensor projections for the optimally discriminating weighting. This localization can be compared to the functional neuroanatomy, serving as a validation of the data driven linear methods. In all three examples, the activity distribution correlated with the source that optimizes single-trial discrimination localizes to a region that is consistent with the functional neuroanatomy. This is important, for instance in order to determine whether the discrimination model is capturing information directly related to the underlying task-dependent cortical activity, or is instead exploiting an indirect cortical response or other physiological signals correlated with the task (e.g. correlations with the stimulus, eye movements, etc.). Localization of the discriminating component activity and its correlates also enables one to determine the neuroanatomical correlations between different discrimination tasks, as was demonstrated for explicit and imagined motor responses in EEG.

While this invention has been described with reference to several illustrative examples and embodiments, they should not be interpreted as limiting the scope or spirit of the invention. In actual practice many modifications may be made by those of ordinary skill in the art without deviating from the scope of the invention as expressed in the appended claims. For example, the system and method of the present invention may be applied to other encephalographic modalities with linear superposition of activity, such as functional infrared imaging (Boas et al., "Imaging the body with diffuse optical tomography," *IEEE Signal Processing Magazine*, 18(6): 57-75, (2001)).

APPENDIX A function [p]=bernoull(x,eta);
% [p] = bernoull(x,eta)
%
% computes Bernoulli distribution of x for "natural parameter" eta.
% The mean m of a Bernoulli distributions relates to eta as,
% m = exp(eta)/(1+exp(eta));

APPENDIX A

```
p = exp(eta.*x - log(1+exp(eta)));
function [v] = logist(x,y,v,show,lambda)
% [v] = logist(x,y,vinit,show,lambda)
% iterative recurcive least squares algorithm for linear logistic model
%
% x - N input samples [N,D]
% y - N binary labels {0,1}
% vinit - initialization for faster convergence (optional)
% show - fi >0 will show something (optional)
% labda - regularization constant for weight decay. Makes logistic
% regression into a support vector machine (cf. Clay Spence). Defaults
% to 10^-6
%
% v - v(1:D) normal to separating hyperplane. v(D+1) slope
%
% compute probability of new samples with p = bernoull(1,[x 1]*v);
[N,D]=size(x);
x = [x ones(N,1)];
if nargin<3 | isempty(v), v = zeros(D+1,1); end;
if nargin<4 | isempty(show); show=0; end;
if nargin<5 | isempty(lambda); lambda=10^-6; end;
% init termination criteria
vold=ones(size(v));
count=0;
% IRLS for binary classification of experts (bernoulli distr.)
while 1
    vold=v;
    mu = bernoull(1,x*v);    % recompute weights
    w = mu.*(1-mu);
    e = (y - mu);
    grad = x'*e - lambda * v;
    %inc = inv(x'*diag(w)*x+eps*eye(D+1)) * grad;
    inc = inv(x'*(repmat(w,1,D+1).*x)+lambda*eye(D+1)) * grad;
    % avoid funny outliers that happen with inv
    if norm(inc)>=1000,
        warning('Bad conditioning. Suggest to encrease regularization constant lambda');
        break;
    end;
    % update
    v = v + inc;
    % exit if converged
    if subspace(v,vold)<10^-7, break, end;
    % exit if its taking to long
    count=count+1;
    if count>100,
        warning('Not converged after 100 iterations.');
        break;
    end;
end;
if show
    subplot(1,2,1)
    ax=[min(x(:,1)), max(x(:,1)), min(x(:,2)), max(x(:,2))];
    plot(x(y>0,1),x(y>0,2),'*',x(y<1,1),x(y<1,2),'+');
    hold on;
    if norm(v)>0,
        tmean=mean(x);
        tmp = tmean; tmp(1)=0; t1=tmp; t1(2)=ax(3); t2=tmp; t2(2)=ax(4);
        xmin=median([ax(1), -(t1*v)/v(1), -(t2*v)/v(1)]);
        xmax=median([ax(2), -(t1*v)/v(1), -(t2*v)/v(1)]);
        tmp = tmean; tmp(2)=0; t1=tmp; t1(1)=ax(1); t2=tmp; t2(1)=ax(2);
        ymin=median([ax(3), -(t1*v)/v(2), -(t2*v)/v(2)]);
        ymax=median([ax(4), -(t1*v)/v(2), -(t2*v)/v(2)]);
        if v(1)*v(2)>0, tmp=xmax;xmax=xmin;xmin=tmp;end;
        if ~(xmin<ax(1)|xmax>ax(2)|ymin<ax(3)|ymax>ax(4)),
            plot([xmin xmax],[ymin ymax]);
        end;
    end;
    hold off;
    subplot(1,2,2);
    vnorm(count) = subspace(v,vold);
    plot(log(vnorm)/log(10))
    drawnow;
end;
end;
function [p]=bernoull(x,eta);
% [p] = bernoull(x,eta)
%
% Computes Bernoulli distribution of x for "natural parameter" eta.
```

-continued

APPENDIX A

```
% The mean m of a Bernoulli distributions relates to eta as,
% m = exp(eta)/(1+exp(eta));
p = exp(eta.*x − log(1+exp(eta)));
clear all
file = '/tmp/tmp';
before = 200; % in ms
after = 500; % in ms
% baseline window
offsetb = 40; % in ms
windowb = 100; % in ms
offset = 140; % in ms
window = 100; % in ms
% baseline window
offsetb = 90; % in ms
windowb = 100; % in ms
offset = 230; % in ms
window = 150; % in ms
% read header from first file (D, fs, and gain are all the same)
[D,N,fs,gain] = readheader(file);
% convert into smaples
before = round(before/1000*fs);
after = round(after/1000*fs);
L = round(window/1000*fs);
offset = round(offset/1000*fs);
Lb = round(windowb/1000*fs);
offsetb = round(offsetb/1000*fs);
% read events and compute transitions
events=readchannels(file,D)−1;
events(2:end) = events(2:end).*(events(1:end−1)~=events(2:end));
e_indx = find((163<=events&events<=167)|events==188|events==189);
c_indx = find(events==162|events==168|events==187);
p_indx = find(events==193); % plane entering the screen
% number of error/correct events per block
blkstart=find(events==161);blkstart(end+1)=length(events);
for i=1:size(blkstart)−1
    e_blk{i} = find(blkstart(i)<e_indx & e_indx<blkstart(i+1));
    c_blk{i} = find(blkstart(i)<c_indx & c_indx<blkstart(i+1));
    p_blk{i} = find(blkstart(i)<p_indx & p_indx<blkstart(i+1));
end
clear events;
% read data around correct and error responces
fid = fopen([file '.bin'],'r','b');
N1=length(e_indx);
for i=1:N1
    fseek(fid,2*D*(e_indx(i)−1−before),−1);
    tmp = fread(fid,[D before+after],'int16');
    error(:,:,i) = tmp(1:D−1,:);
end
N2=length(c_indx);
for i=1:N2
    fseek(fid,2*D*(c_indx(i)−1−before),−1);
    tmp = fread(fid,[D before+after],'int16');
    correct(:,:,i) = tmp(1:D−1,:);
end
fclose(fid);
N=N1+N2
T=before+after;
time = ((1:T)−before)/fs;
% baseline the data
if windowb
    error   = error   − repmat(mean( error(:,before+offsetb+(1:Lb),:),2),[1 T 1]);
    correct = correct − repmat(mean(correct(:,before+offsetb+(1:Lb),:),2),[1 T 1]);
end
% show trial averaged leads
figure(1);
subplot(2,1,1); plot(time,mean(error,3)');
ax=axis; hold on;
plot([0 0],ax(3:4),'k');
plot(time(before+offset)*[1 1],ax(3:4),'g')
plot(time(before+offset+L)*[1 1],ax(3:4),'g')
plot(time(before+offsetb)*[1 1],ax(3:4),'b')
plot(time(before+offsetb+Lb)*[1 1],ax(3:4),'b')
hold off;
subplot(2,1,2); plot(time,mean(correct,3)');
ax=axis; hold on;
plot([0 0],ax(3:4),'k');
plot(time(before+offset)*[1 1],ax(3:4),'g')
```

APPENDIX A

```
plot(time(before+offset+L)*[1 1],ax(3:4),'g')
plot(time(before+offsetb)*[1 1],ax(3:4),'b')
plot(time(before+offsetb+Lb)*[1 1],ax(3:4),'b')
hold off; drawnow;
% logistic regression
z = [zeros(N1*L,1);ones(N2*L,1)];
x = cat(3, ...
        error(:,before+offset+(1:L),:),...
        correct(:,before+offset+(1:L),:));
x = x-repmat(mean(mean(x,2),3),[1 L N1+N2]);
% do logistic regression on all the data
v = logist(x(:,:)',z);
y = x(:,:)'*v(1:end-1)+v(end);
u = y\(x(:,:)')*norm(v(1:end-1));
figure(2);
S = reshape(v(1:end-1)'*error(:,:),[T N1]);
S2 = reshape(v(1:end-1)'*correct(:,:),[T N2]);
subplot(1,3,1);
plot(time,mean(S,2),'b'); hold on;
plot(time,mean(S2,2),'r');
plot(time,[mean(S,2)+std(S,[ ],2),mean(S,2)-std(S,[ ],2)],':b');
plot(time,[mean(S2,2)+std(S2,[ ],2),mean(S2,2)-std(S2,[ ],2)],':r');
ax = axis;
plot([0 0],ax(3:4),'k');
plot(time(before+offset)*[1 1],ax(3:4),'g');
plot(time(before+offset+L)*[1 1],ax(3:4),'g');
plot(time(before+offsetb)*[1 1],ax(3:4),'b')
plot(time(before+offsetb+Lb)*[1 1],ax(3:4),'b')
axis('tight'); hold off
axis('square')
title('discriminating component')
xlabel('time in s')
subplot(1,3,2);
topoplot(u(2:61),'cap60cent.loc','electrodes','off','style','straight','maplimits','maxmin');
title('scalp projection')
axis('square')
subplot(1,3,3);
y = reshape(v'*[x(:,:); ones(1,N*L)],L,N);
ymean=mean(y);
p = bernoull(1,ymean);
z=[zeros(N1,1);ones(N2,1)];
rocarea(p,z);
axis('square')
pause(3)
drawnow
figure(5)
warning off
subplot(2,1,1)
K=length(blkstart)-1;
clear blk_N blk_mean blk_std
for i=1:K
    indx = e_blk{i};
    blk_N(i) = length(indx);
    blk_mean(i) = mean(mean(y(:,indx)));
    blk_std(i) = std(mean(y(:,indx)));
    blk_Np(i) = length(p_blk{i});
end
bar(3-blk_mean); hold on
errorbar(3-blk_mean,blk_std./sqrt(blk_N),'.g'); hold off
set(gca,'XTick',1:length(blk_Np));
set(gca,'XTickLabel',blk_Np);
ax=axis; axis([0 length(blk_Np)+1 ax(3:4)]);
xlabel('number of tracks in wave')
title('warning detector magnitude')
ylabel('detector magnitude')
subplot(2,2,3)
clear blkp_std blkp_N blkp_mean
for i=1:max(blk_Np)
    indx = find(blk_Np==i);
    if length(indx)==0,
        blkp_N(i)    = NaN;
        blkp_mean(i) = NaN;
        blkp_std(i)= NaN;
    else,
        tmp=blk_mean(indx); tmp=tmp(find(tmp~=NaN));
        blkp_N(i)    = length(tmp);
        blkp_mean(i) = mean(tmp);
```

-continued

APPENDIX A

```
        blkp_std(i)= std(tmp);
    end
end
bar(3-blkp_mean); hold on;
errorbar(3-blkp_mean,blkp_std./sqrt(blkp_N),'.g'); hold off
xlabel('number of traks in wave')
ylabel('detector magnitude')
subplot(2,2,4)
clear blke_std blke_N blke_mean
for i=1:max(blk_N)
    indx = find(blk_N==i);
    if length(indx)==0,
        blke_N(i)   = NaN;
        blke_mean(i) = NaN;
        blke_std(i)= NaN;
    else,
        tmp=blk_mean(indx); tmp=tmp(find(tmp~=NaN));
        blke_N(i)   = length(tmp);
        blke_mean(i) = mean(tmp);
        blke_std(i)= std(tmp);
    end
end
bar(3-blke_mean); hold on
errorbar(3-blke_mean,blke_std./sqrt(blke_N),'.g'); hold off
ax=axis; axis([0 length(blke_mean)+1 ax(3:4)]);
xlabel('number of warnings in wave')
ylabel('detector magnitude')
warning off
% leave-one out performance
zloo=[zeros(N1,1);ones(N2,1)]; % 1 label per button push
ploo=p;
figure(4);clf
i=1; if i==1, clear vloo; end;
for i=i:length(zloo)
    indx=ones(N,1); indx(i)=0;
    tmp = x(:,:,find(indx));
    vloo(:,i)=logist(tmp(:,:)',kron(zloo(find(indx)),ones(L,1)),v);
    y = [x(:,:,i)' ones(L,1)]*vloo(:,i);
    ymean = mean(reshape(y,L,1));
    ploo(i) = bernoull(1,ymean);
    plot(p, 'b'); hold on; plot(ploo,'r');   hold off;
    [Az,Ry,Rx]=rocarea(ploo,zloo);
    disp(num2str([i Az]));
    drawnow
end;
figure(2)
rocarea(ploo,zloo);
```

We claim:

1. A method for interpreting brain activity comprising the steps of:
    attaching a high-density array of brain activity sensors to a subject;
    prompting said subject with an external stimulus;
    generating a response signal from each of said sensors at a predetermined point in time with reference to the occurrence of said prompting;
    computing a respective spatial weighting coefficient corresponding to each of said sensors by applying a linear classifier to said predetermined number of response signals;
    weighting each response signal in accordance with its corresponding weighting coefficient; and
    linearly integrating the weighted response signals whereby a single output signal is generated, said output signal having a relatively high correlation to the brain activity of said subject in response to said external stimulus.

2. The method of claim 1 wherein said weighting coefficients are computed such that the weighted responses are maximally discriminating between first and second predetermined times corresponding to two stimuli where a maximum difference in brain activity is expected.

3. The method of claim 2 wherein the linear integration is a summation.

4. The method of claim 2 wherein said brain activity sensors are EEG sensors.

5. The method of claim 2 wherein said brain activity sensors are MEG sensors.

6. The method of claim 2 wherein said stimulus is visual.

7. The method of claim 1 further comprising the steps of:
    identifying an expected scalp locality for discriminating components of the output signal relative to the external stimulus;
    computing a sensor projection for each of said sensors;
    using said sensor projections to identify the scalp locality for the actual discriminating components for said external stimulus; and
    evaluating the validity of said output signal by determining whether the identified locality for the actual discriminating components is substantially the same as the expected locality.

8. A system for interpreting brain activity comprising:

a high-density array of brain activity sensors for application to the head of a subject; and a computer for receiving signals from said sensors, said computer programmed to:

compute a respective spatial weighting coefficient corresponding to each of said sensors by applying a linear classifier to signals generated by said sensors in response to an external stimulus, weight each of said signals in accordance with its corresponding weighting coefficient, and linearly integrate the weighted response signals, whereby a single output signal is generated, said output signal having a relatively high correlation to the brain activity of said subject in response to said external stimulus.

9. The system of claim 8 further comprising a feedback display.

10. The system of claim 9 wherein said feedback display provides said external stimulus.

11. The system of claim 8 wherein said weighting coefficients are computed such that the weighted responses are maximally discriminating between first and second predetermined times corresponding to two stimuli where a maximum difference in brain activity is expected.

12. The system of claim 11 wherein said brain activity sensors are EEG sensors.

13. The system of claim 11 wherein said brain activity sensors are MEG sensors.

14. The system of claim 8 wherein said linear integration is a summation.

* * * * *